US010617872B2

(12) United States Patent
Marnfeldt

(10) Patent No.: US 10,617,872 B2
(45) Date of Patent: Apr. 14, 2020

(54) SYSTEMS AND METHODS FOR PROGRAMMING NEUROMODULATION THERAPY

(71) Applicant: Boston Scientific Neuromodulation Corporation, Valencia, CA (US)

(72) Inventor: Goran N. Marnfeldt, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 242 days.

(21) Appl. No.: 15/790,642

(22) Filed: Oct. 23, 2017

(65) Prior Publication Data

US 2018/0140845 A1 May 24, 2018

Related U.S. Application Data

(60) Provisional application No. 62/425,848, filed on Nov. 23, 2016.

(51) Int. Cl.
*A61N 1/36* (2006.01)
*A61N 1/365* (2006.01)
(Continued)

(52) U.S. Cl.
CPC ....... *A61N 1/36189* (2013.01); *A61N 1/0551* (2013.01); *A61N 1/365* (2013.01);
(Continued)

(58) Field of Classification Search
CPC .............. A61N 1/36189; A61N 1/0551; A61N 1/3605; A61N 1/36114; A61N 1/36146;
(Continued)

(56) References Cited

U.S. PATENT DOCUMENTS 7,650,184 B2 1/2010 Walter
8,019,439 B2 9/2011 Kuzma et al.
(Continued)

FOREIGN PATENT DOCUMENTS

WO WO-2018097917 A1 5/2018
WO WO-2018097918 A1 5/2018

OTHER PUBLICATIONS

"U.S. Appl. No. 15/790,977, Non Final Office Action dated Feb. 20, 2019", 10 pgs.
(Continued)

*Primary Examiner* — Carl H Layno
*Assistant Examiner* — Erin M Piateski
(74) *Attorney, Agent, or Firm* — Schwegman Lundberg & Woessner, P.A.

(57) ABSTRACT

This document discusses, among other things, systems and methods for programming a neuromodulation therapy to treat neurological or cardiovascular diseases. A system includes an ambulatory medical device (AMD) and at least one computer-readable storage medium including instructions executable on an external system. The instructions, when executed by the external system, causes a user interface in the external system to receive a waveform function and one or more modulation parameter values. The waveform function includes one or more modulation programs characterized by one or more modulation parameters. The instructions causes a compiler to translate the waveform function into virtual machine (VM) instructions, which can be transmitted to the AMD. The AMD includes a VM that executes the VM instructions, and generates one or more modulation waveform datasets. The AMD may generate and deliver electrostimulation therapy in accordance with the one or more modulation waveform datasets.

20 Claims, 7 Drawing Sheets

(51) Int. Cl.
- *A61N 1/37* (2006.01)
- *A61N 1/05* (2006.01)
- *A61N 1/362* (2006.01)
- *A61N 1/372* (2006.01)

(52) U.S. Cl.
CPC ......... *A61N 1/3605* (2013.01); *A61N 1/3627* (2013.01); *A61N 1/36114* (2013.01); *A61N 1/36146* (2013.01); *A61N 1/3712* (2013.01); *A61N 1/37264* (2013.01); *A61N 1/36071* (2013.01); *A61N 1/37247* (2013.01); *A61N 1/37276* (2013.01)

(58) Field of Classification Search
CPC .... A61N 1/3627; A61N 1/365; A61N 1/3712; A61N 1/37264; A61N 1/36071; A61N 1/37247; A61N 1/37276
USPC .......................................................... 607/11
See application file for complete search history.

(56) References Cited

U.S. PATENT DOCUMENTS

| | | | |
|---|---|---|---|
| 9,358,396 B2 | 6/2016 | Holley | |
| 10,441,781 B2 | 10/2019 | Marnfeldt et al. | |
| 2001/0007950 A1 | 7/2001 | North et al. | |
| 2012/0197336 A1 | 8/2012 | Su | |
| 2014/0277267 A1* | 9/2014 | Vansickle | A61N 1/36071 607/46 |
| 2015/0032181 A1 | 1/2015 | Baynham et al. | |
| 2015/0165202 A1 | 6/2015 | Grandhe | |
| 2015/0217116 A1 | 8/2015 | Parramon et al. | |
| 2016/0082252 A1 | 3/2016 | Hershey et al. | |
| 2016/0303376 A1 | 10/2016 | Dinsmoor et al. | |
| 2017/0173335 A1* | 6/2017 | Min | A61N 1/36071 |
| 2018/0140830 A1 | 5/2018 | Marnfeldt et al. | |

OTHER PUBLICATIONS

"U.S. Appl. No. 15/790,977, Notice of Allowance dated Jun. 12, 2019", 7 pgs.

"U.S. Appl. No. 15/790,977, Response filed May 13, 2019 to Non Final Office Action dated Feb. 20, 2019", 10 pgs.

"International Application Serial No. PCT/US2017/057851, International Preliminary Report on Patentability dated Jun. 6, 2019", 8 pgs.

"International Application Serial No. PCT/US2017/057851, International Search Report dated Feb. 16, 2018", 4 pgs.

"International Application Serial No. PCT/US2017/057851, Written Opinion dated Feb. 16, 2018", 6 pgs.

"International Application Serial No. PCT/US2017/057912, International Preliminary Report on Patentability dated Jun. 6, 2019", 8 pgs.

"International Application Serial No. PCT/US2017/057912, International Search Report dated Feb. 16, 2018", 5 pgs.

"International Application Serial No. PCT/US2017/057912, Written Opinion dated Feb. 16, 2018", 8 pgs.

U.S. Appl. No. 15/790,977 U.S. Pat. No. 10/441,781, filed Oct. 23, 2017, Systems and Methods for Programming Neuromodulation Waveform.

U.S. Appl. No. 16/556,730, filed Aug. 30, 2019, Systems and Methods for Programming Neuromodulation Waveform.

* cited by examiner

SYSTEMS AND METHODS FOR PROGRAMMING NEUROMODULATION THERAPY

CLAIM OF PRIORITY

This application claims the benefit of priority under 35 U.S.C. § 119(e) of U.S. Provisional Patent Application Ser. No. 62/425,848, filed on Nov. 23, 2016, which is herein incorporated by reference in its entirety.

CROSS REFERENCE TO RELATED APPLICATIONS

This application is related to commonly assigned U.S. Provisional Patent Application Ser. No. 62/425,855, entitled "SYSTEMS AND METHODS FOR PROGRAMMING NEUROMODULATION WAVEFORM", filed on Nov. 23, 2016, which is incorporated herein by reference in its entirety.

TECHNICAL FIELD

This document relates generally to medical systems, and more particularly, but not by way of limitation, to systems, devices, and methods for programming neuromodulation therapy.

BACKGROUND

Neuromodulation, also referred to as neurostimulation, has been proposed as a therapy for a number of conditions. Examples of neuromodulation include Spinal Cord Stimulation (SCS), Deep Brain Stimulation (DBS), Peripheral Nerve Stimulation (PNS), and Functional Electrical Stimulation (FES). For example, SCS has been used to treat chronic pain syndromes. Some neural targets may be complex structures with different types of nerve fibers. An example of such a complex structure is the neuronal elements in and around the spinal cord targeted by SCS.

Implantable neuromodulation systems have been applied to deliver such a therapy. An implantable neuromodulation system may include an implantable neuromodulator, also referred to as an implantable pulse generator (IPG), and one or more implantable leads each including one or more electrodes. The implantable neuromodulator delivers neuromodulation energy through one or more electrodes placed on or near a target site in the nervous system. An external programming device may be used to program the implantable neuromodulator with stimulation parameters controlling the delivery of the neuromodulation energy.

Electrical stimulation energy may be delivered from the implantable neuromodulator to the electrodes to stimulate neural tissue in the form of an electrical pulsed waveform. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses provided through the electrode array. Each electrode configuration, along with the electrical pulse parameters, constitutes a modulation parameter set for use in an electrostimulation therapy.

SUMMARY

Programming of neuromodulation therapy, such as SCS, conventionally involves separate and independent programming of each of a multitude of modulation parameters such as parameters that define a modulation waveform. Some neuromodulation systems may include electrostimulation configuration and complex modulation waveforms. These modulation waveforms may be characterized by a large amount of modulation parameters. Programming of the neuromodulation therapy may require adjusting these modulation parameters individually and separately, and transmitting the modulation parameters to an IPG. This may put a burden on a telemetry system that enables communications between the IPG and the programming device.

Interpretation and execution of a large amount of the modulation parameters at the IPG can be complicated. Some neuromodulation system may enable a user to create arbitrary modulation waveforms. The modulation waveform may comprise multiple pulses with distinct shapes or morphology, as characterized by distinct pulse amplitudes, pulse widths, pulse rates, or other pulse morphological parameters. The modulation parameters, when transmitted from a programming device to the IPG, are typically interpreted by firmware on the IPG. Interpretation and execution of instructions for adjusting modulation waveform may require intensive firmware access such as to various registers for individual modulation parameters. As such, large amount of modulation parameters would substantially increase the complexity of the firmware on the IPG. Furthermore, it is desirable in some occasions to modify the modulation waveforms by updating modulation parameters to meet patient needs. When the firmware is exposed to frequent modulation parameter updates, it may be more susceptible to inadvertent mistakes introduced by waveform modification. On top of the potential elevated risk to IPG system security, additional firmware revalidation may be required. With these issues in mind, the present inventors have recognized that there remains a demand for systems and methods to more efficiently program an electrostimulation system for delivering electrostimulation therapy.

Example 1 is a system for providing electrostimulation to a patient. The system comprises an ambulatory medical device (AMD) including a virtual machine (VM) and an electrostimulator, and at least one computer-readable storage medium including instructions executable on an external system communicatively coupled to the AMD. The external system comprises a user interface, a compiler, and a telemetry circuit. The instructions, when executed by the external system, may cause the user interface to receive (1) a waveform function defining one or more modulation programs characterized by respective one or more modulation parameters, and (2) a user input of values for the one or more modulation parameters of the one or more modulation programs. The instruction may also cause the compiler to translate the waveform function into VM instructions, and cause the telemetry circuit to transmit the VM instructions to the AMD. The VM of the AMD may be configured to execute the VM instructions to generate respective one or more modulation waveform datasets corresponding to the one or more modulation programs. The electrostimulator may be configured to generate electrostimulation therapy according to the one or more modulation waveform datasets.

In Example 2, the subject matter of Example 1 optionally includes the external system that is configured to modify the waveform function or adjust the values for the one or more modulation parameters. The compiler is configured to translate the modified waveform function into modified VM instructions. The VM of the AMD is configured to update the one or more modulation waveform datasets by executing the modified VM instructions or by using the adjusted values for the one or more modulation parameters.

In Example 3, the subject matter of any one or more of Examples 1-2 optionally further includes the external system that may include: a device programmer including the user interface to receive the waveform function and the compiler to translate the waveform function into the VM instructions; and a remote control device including a user input device to receive the user input of the values for the one or more modulation parameters.

In Example 4, the subject matter of any one or more of Examples 1-3 optionally includes the electrostimulator that is configured to generate a spinal cord stimulation therapy or a deep brain stimulation therapy.

In Example 5, the subject matter of any one or more of Examples 1-4 optionally includes the electrostimulator that is configured to generate a cardiac stimulation therapy or a neural stimulation therapy to treat a cardiovascular disease.

In Example 6, the subject matter of any one or more of Examples 1-5 optionally includes the user interface that may include a display configured to textually or graphically display the waveform function.

In Example 7, the subject matter of any one or more of Examples 1-6 optionally includes the waveform function that may define one or more modulation programs characterized by a respective one or more temporal modulation parameters comprising at least one of: a pulse amplitude; a pulse width; a pulse frequency; or a burst intensity.

In Example 8, the subject matter of any one or more of Examples 1-7 optionally further includes the VM of the AMD that is configured to execute the VM instructions to generate a dataset of a multiphasic modulation waveform corresponding to a modulation program.

In Example 9, the subject matter of any one or more of Examples 1-8 optionally includes the waveform function that further includes instructions for computing delivered energy or charge balance associated with the one or more modulation waveform datasets corresponding to the one or more modulation programs.

In Example 10, the subject matter of any one or more of Examples 1-9 optionally includes the AMD that further includes a sensor circuit configured for sensing a physiological response to a delivery of the electrostimulation therapy according to the one or more modulation waveform datasets. The waveform function further includes instructions for modifying one or more modulation programs based on the sensed physiological response.

In Example 11, the subject matter of Example 10 optionally includes the AMD that further includes a pain analyzer configured to generate a pain score using the sensed physiological response. The waveform function further includes instructions for modifying one or more modulation programs based on the generated pain score.

In Example 12, the subject matter of any one or more of Examples 1-11 optionally includes the user interface that is configured to receive a user input of a modulation magnitude representing a level of stimulation intensity. The values for the one or more modulation parameters may be determined based on the modulation magnitude.

In Example 13, the subject matter of Example 12 optionally includes the external system that further comprises a magnitude interpreter unit configured to translate the modulation magnitude into the values for the one or more modulation parameters using a plurality of gain functions respectively defining values of the one or more modulation parameters corresponding to a plurality of modulation magnitudes.

In Example 14, the subject matter of Example 13 optionally includes the magnitude interpreter unit that is at least partially included in the external system or the AMD.

In Example 15, the subject matter of any one or more of Examples 1-14 optionally includes the VM that is further configured to selectively authorize access to one or more registers for electrostimulation therapy generation.

Example 16 is a method for providing electrostimulation to a patient via an ambulatory medical device (AMD) communicatively coupled to an external system. The method comprises steps of: establishing a waveform function via an external system, the waveform function defining one or more modulation programs characterized by respective one or more modulation parameters; receiving a user input of values for the one or more modulation parameters of the one or more modulation programs; translating, via a compiler included in the external system, the waveform function into virtual machine (VM) instructions; transmitting the VM instructions to the AMD; executing the VM instructions to generate respective one or more modulation waveform datasets corresponding to the one or more modulation programs; and generating electrostimulation therapy via the AMD according to the one or more modulation waveform datasets.

In Example 17, the subject matter of Example 16 optionally includes steps of modifying the waveform function or adjusting the values for the one or more modulation parameters, and updating one or more of the modulation waveform datasets using (1) VM instructions translated from the modified waveform function or (2) adjusted values for the one or more modulation parameters.

In Example 18, the subject matter of any one or more of Examples 16-17 optionally includes the electrostimulation therapy that includes at least one of a spinal cord stimulation therapy, a deep brain stimulation therapy, a cardiac stimulation therapy, or a vagus nerve stimulation therapy.

In Example 19, the subject matter of any one or more of Examples 16-18 optionally includes the step of establishing the waveform function that includes receiving a textual or graphical description of the one or more modulation programs.

In Example 20, the subject matter of any one or more of Examples 16-19 optionally include the established waveform function that further includes instructions for computing delivered energy or charge balance associated with the one or more modulation waveform datasets corresponding to the one or more modulation programs.

In Example 21, the subject matter of any one or more of Examples 16-20 optionally includes steps of: sensing a physiological response to a delivery of the electrostimulation therapy according to the modulation waveform dataset; and generating a pain score using the sensed physiological response; wherein the waveform function further includes instructions for modifying one or more modulation programs based on the generated pain score.

In Example 22, the subject matter of any one or more of Examples 16-21 optionally includes a step of receiving a user input of values for the one or more modulation parameters includes receiving a modulation magnitude representing a level of stimulation intensity. The values for the one or more modulation parameters may be determined based on the modulation magnitude.

This summary is intended to provide an overview of subject matter of the present patent application. It is not intended to provide an exclusive or exhaustive explanation of the disclosure. The detailed description is included to provide further information about the present patent application. Other aspects of the disclosure will be apparent to persons skilled in the art upon reading and understanding the following detailed description and viewing the drawings that form a part thereof, each of which are not to be taken in a limiting sense.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
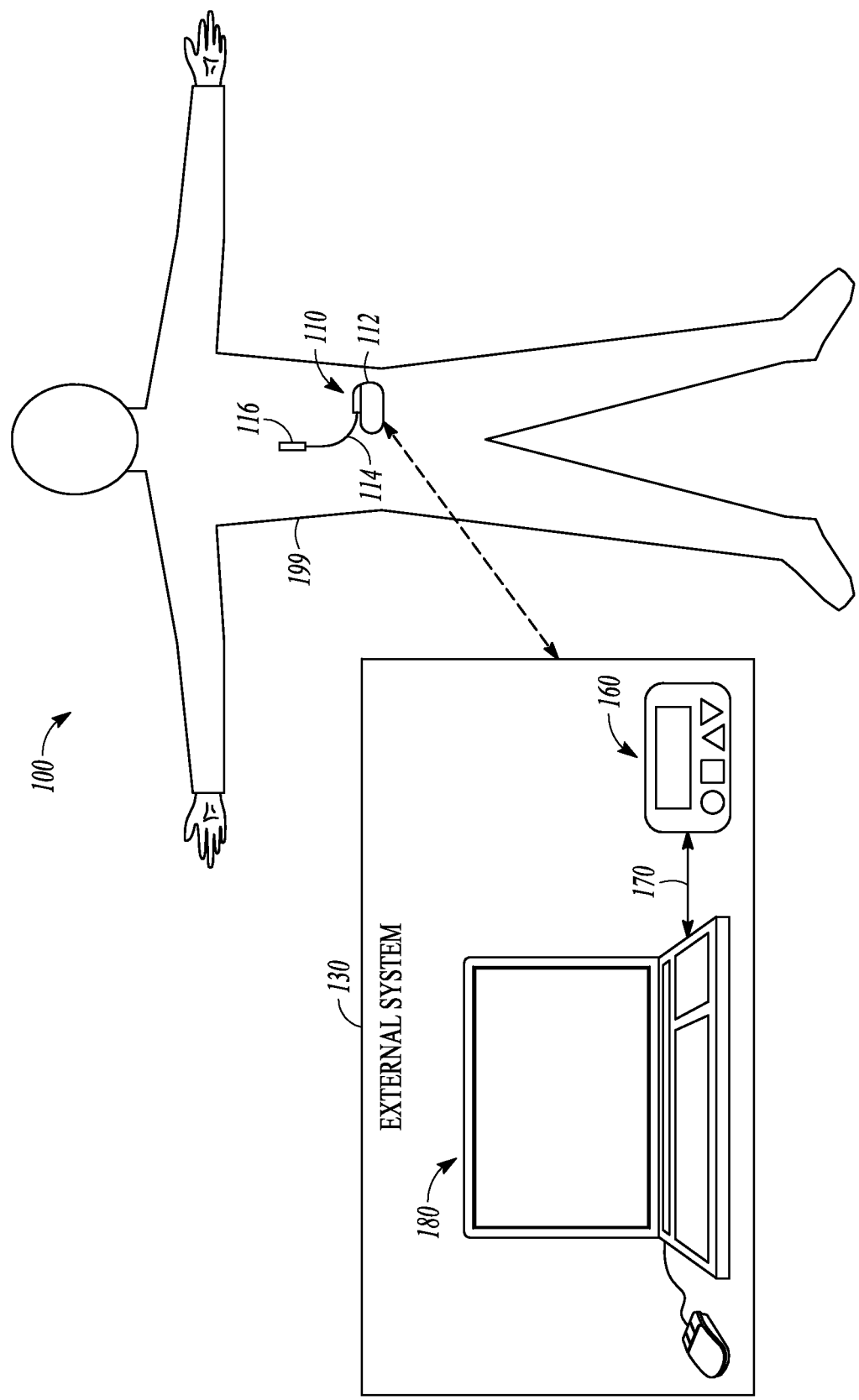
FIG. 1 illustrates, by way of example and not limitation, a neuromodulation system and portions of an environment in which the neuromodulation system may operate.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

Advancements in neuroscience and neuromodulation research have led to a demand for using complex and/or individually optimized patterns of neuromodulation energy for various types of therapies. Disclosed herein are systems, devices, and methods for programming neuromodulation and providing therapy to a patient. In various embodiments, the present system may include an ambulatory medical device (AMD), such as an implantable neuromodulator device, and an external system in communication with the AMD. The AMD may include a virtual machine (VM) for interpreting programming instructions received from the external system. The external system may include a user interface to receive a waveform function that defines one or more modulation programs characterized by respective modulation parameters, and to receive user input of modulation parameter values. The external system may include a compiler that translates the waveform function into virtual machine (VM) instructions. The VM instructions may be transmitted via a telemetry circuit to the IMD for execution by the VM, which generates one or more modulation waveform datasets corresponding to the modulation programs. The AMD may generate and deliver electrostimulation therapy in accordance with the one or more modulation waveform datasets to treat a neurological or cardiovascular disorder.

The present system may be implemented using a combination of hardware and software designed to provide neuromodulation therapy to increase therapeutic efficacy, increase patient satisfaction for neuromodulation therapies, reduce side effects, and/or increase device longevity. The present system may be applied in any neuromodulation (neuromodulation) therapies, including but not limited to SCS, DBS, PNS, FES, and Vagus Nerve Stimulation (VNS) therapies. With the waveform function and the VM, the present system in the present system is advantageous in managing complex stimulation waveforms in a safe and systematic way. VM resides in a sandboxed environment in the AMD, and isolates the access to the stimulation-related registers from the rest of the system, thereby protecting the system from inadvertent mistakes, while at the same time allowing new stimulation functions and behavior to be implemented without modifying or revalidating the AMD firmware.

FIG. 1 illustrates, by way of example and not limitation, a neuromodulation system 100 and portions of an environment in which the neuromodulation system 100 may operate. The neuromodulation system 100 may include an ambulatory system 110, and at least one computer-readable storage medium. The at least one computer-readable storage medium may include instructions executable on an external system 130 communicatively coupled to the ambulatory system 110 via a communication link 120. In an example, the external system 130 may be included in the neuromodulation system 100.

The ambulatory system 110, configured to be associated with a body 199 of a patient, may include an ambulatory device such as an implantable medical device (IMD) 112, a lead system 114, and one or more electrodes 116. The IMD 112 may be configured to generate one or more energy modalities for delivery to target tissues for medical diagnosis, or to achieve desired therapeutic effects such as to modify, restore, or improve the patient's neural or cardiac function. Examples of the energy modalities may include electrical, magnetic, or other forms of energy.

In an example, the IMD 112 may include a hermetically sealed can, which houses sensing circuitry, electrostimulation circuitry, control circuitry, communication circuitry, and a battery, among other components. The sensing circuitry of the IMD 112 may sense physiological or functional signals from the patient via electrodes 116 or various types of ambulatory sensors associated with the patient. The sensing electrodes or the ambulatory sensors may be included within, or otherwise in wired or wireless connection with, the IMB 112. In an example, the IMB 112 may be an implantable neuromodulator device (IND) configured to provide SCS, DBS, PNS, or other types of neuromodulation therapies. The electrostimulation circuitry may generate electrostimulation pulses to stimulate a neural target via the electrodes 116. In an example, the electrodes 116 may be positioned on or near a spinal cord, and the electrostimulation circuitry may be configured to deliver SCS to treat pain or other disorders. In another example, the electrodes 116 may be surgically placed at other neural targets such as a brain or a peripheral neutral tissue, and the electrostimulation circuitry may be configured to deliver brain or peripheral stimulation to treat epilepsy, chronic pain, obsessive compulsive disorder, tremor, Parkinson's disease, or dystonia, among other movement and affective disorders. The IMB 112 may additionally or alternatively include an implantable cardiac device coupled to electrodes positioned at a target cardiovascular tissue or a target neural tissue, and the IMD 112 may sense cardiac activities or generate a cardiac stimulation therapy or a neural stimulation therapy to treat a cardiovascular disease.

In various examples, the electrodes 116 may be distributed in one or more leads of the lead system 114 electrically coupled to the IMD 112. In an example, the lead system 114 may include a directional lead that includes at least some segmented electrodes circumferentially disposed about the directional lead. Two or more segmented electrodes may be distributed along a circumference of the lead. The actual number and shape of leads and electrodes may vary according to the intended application. Detailed description of construction and method of manufacturing percutaneous stimulation leads are disclosed in U.S. Pat. No. 8,019,439, entitled "Lead Assembly and Method of Making Same," and U.S. Pat. No. 7,650,184, entitled "Cylindrical Multi-Contact Electrode Lead for Neural Stimulation and Method of Making Same," the disclosures of which are incorporated herein by reference. The electrodes 116 may provide an electrically conductive contact providing for an electrical interface between the IMD 112 and tissue of the patient. The neuromodulation pulses are each delivered from the IMB 112 through a set of electrodes selected from the electrodes 116. The selected electrodes may form electrode combinations which define the electrodes that are activated as anodes (positive), cathodes (negative), and turned off (zero). Stimulation energy may be fractionalized over the selected active electrodes by defining amount of current, voltage, or energy assigned to the active electrodes. In various examples, multiple individually defined pulses may be included in a neuromodulation waveform, and the set of electrodes may be individually definable by the user for each of the individually defined pulses.

Although the discussion herein with respect to the neuromodulation system 100 focuses on implantable device such as the IMD 112, this is meant only by way of example and not limitation. It is within the contemplation of the inventors and within the scope of this document, that the systems, devices, and methods discussed herein may also be used for programming neuromodulation therapy via subcutaneous medical devices, wearable medical devices, or other external medical devices, or a combination of implantable, wearable, or other external devices.

The external system 130, via a communication link 120, may control the operation of the IMD 112, including programming the IMD 112 with neuromodulation therapies or cardiac therapies. The external system 130 may additionally receive, via the communication link 120, information acquired by the IMB 112, such as one or more physiological or functional signals. In an example, the external system 130 may characterize pain sensed by a patient using the physiological or functional signals received from the IMD 112, and program the IMD 112 to deliver pain therapy in a closed-loop fashion based at least on the pain characterization.

The communication link 120 may include one or more communication channels and intermediate devices between the external system and the IMD, such as a wired link, a telecommunication link such as an internet connection, or a wireless link such as one or more of an inductive telemetry link, a radio-frequency (RF) telemetry link. The communication link 120 may provide for data transmission between the IMB 112 and the external system 130. The transmitted data may include, for example, real-time physiological data acquired by the IMD 112, physiological data acquired by and stored in the IMD 112, therapy history data, data indicating device operational status of the IMD 112, one or more programming instructions to the IMD 112 which may include configurations for sensing physiologic signal or stimulation commands and stimulation parameters, or device self-diagnostic test, among others.

The external system 130 may include a dedicated hardware/software system such as a programmer, a remote server-based patient management system, or alternatively a system defined predominantly by software running on a standard personal computer. By way of example and not limitation, the external system 130 may include a programmer 180 and an intermediate controller 160. The programmer 180 may be communicatively coupled to the IMB 112, such as via a RF telemetry link (not shown). The programmer 180 may enable the system user to program the IMD 112 with the neuromodulation parameters. Examples of the neuromodulation parameters may include electrode combinations that define the electrodes that are activated as anodes (positive), cathodes (negative), and turned off (zero), percentage of stimulation energy assigned to each electrode (fractionalized electrode configurations), and electrical pulse parameters that define the pulse amplitude (which may be measured in milliamps or volts depending on whether the IMB 112 supplies constant current or constant voltage to the electrodes 140), pulse duration (which may be measured in microseconds), pulse rate (which may be measured as pulses per second), and burst intensity (which may be measured as the stimulation "on" duration X and stimulation "off" duration Y). The programming of the IMD 112 may be performed intraoperatively (e.g., during implant of the IMD 112 and/or the leads 130 in an operating room) or during a follow-up visit with the patient. Examples of the internal components of the programmer 180 are discussed below, such as with reference to FIG. 3.

The programmer 180 may alternatively indirectly communicate with the IMD 112 through the intermediate controller 160. The intermediate controller 160 may take the form of a handheld external remote control (RC) device configured to be in communication with the IMB 112 via a bi-directional communications link, such as RF telemetry. Examples of the internal components of the intermediate controller 160 are discussed below, such as with reference to FIG. 2. The intermediate controller 160 may include buttons, touch-screen icons, or other types of actuators to enable a system user to select an operation mode under which the intermediate controller 160 may operate. Non-limiting examples of the operating modes may include a Pulse Amplitude Adjustment Mode, a Pulse Width Adjustment Mode, or a Pulse Rate Adjustment Mode, among other modulation parameter adjustment modes, which respectively allow for individualized and independent adjustment of pulse amplitude, pulse width, or pulse rate of neuromodulation waveform. Alternatively or additionally, the intermediate controller 160 may be placed into a Modulation Magnitude Adjustment Mode, where two or more modulation parameters may be concurrently adjusted using a signal parameter of modulation magnitude. The modulation magnitude may take a unit-less value representing a level of stimulation intensity. The modulation magnitude may control multiple modulation parameters according to respective parameter gain functions (PGFs). Each PGF associates a modulation parameter with the modulation magnitude. The PGFs may be linear, piece-wise linear, or nonlinear functions; thus the modulation parameters may co-vary linearly or nonlinearly with the modulation magnitude. In an example, the pulse amplitude and pulse rate may each be proportional to the modulation magnitude, such that at a higher modulation magnitude, more intensive stimulation strength may be perceived.

In some examples, the intermediate controller 160 may be placed into a Modulation Program Selection Mode, which allows a user to select one from a plurality of modulation programs. Each modulation program may include an aggregation of a plurality of modulation parameters (such as pulse amplitude, pulse width, or pulse rate, among others) with respectively programmed values. The modulation programs may be associated with distinct physiological states or physical activity levels. In an example, the modulation programs may include a modulation program for sleep state, a modulation program for awakening state, and a modulation program for a specified physical activity level.

The intermediate controller 160 may telemetrically control the IMD 112 to generate electrostimulation pulses in accordance with selected stimulation parameters. The programmer 180 may communicate with the intermediate controller 160 via an infrared communications link 170. The neuromodulation parameters provided by the programmer 180 may also be used to program the intermediate controller 160, such that the neuromodulation parameters may be subsequently modified by operation of the intermediate controller 160 without the assistance of the programmer 180. In an example, the programmer 180, either alone or in combination with the intermediate controller 160, may control the operation of the IMD 112, such as turning on or off and programming the IMB 112 with different neuromodulation parameter sets to actively control the characteristics of the electrostimulation output.

In some examples, at least one computer-readable storage medium may be included in the neuromodulation system 100. The at least one computer-readable storage medium can be physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) in the external system 130 to create members of the circuit set in hardware via variable connections to carry out portions of the specific operation when in operation. The instructions stored in the at least one computer-readable storage medium, when executed by the external system, may cause the external system 130 to perform various operations, such as those performed by the programmer 180 or the intermediate controller 160 as discussed above.

Portions of the IMB 112 or the external system 130 may be implemented using hardware, software, firmware, or combinations thereof. Portions of the IMD 112 or the external system 130 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
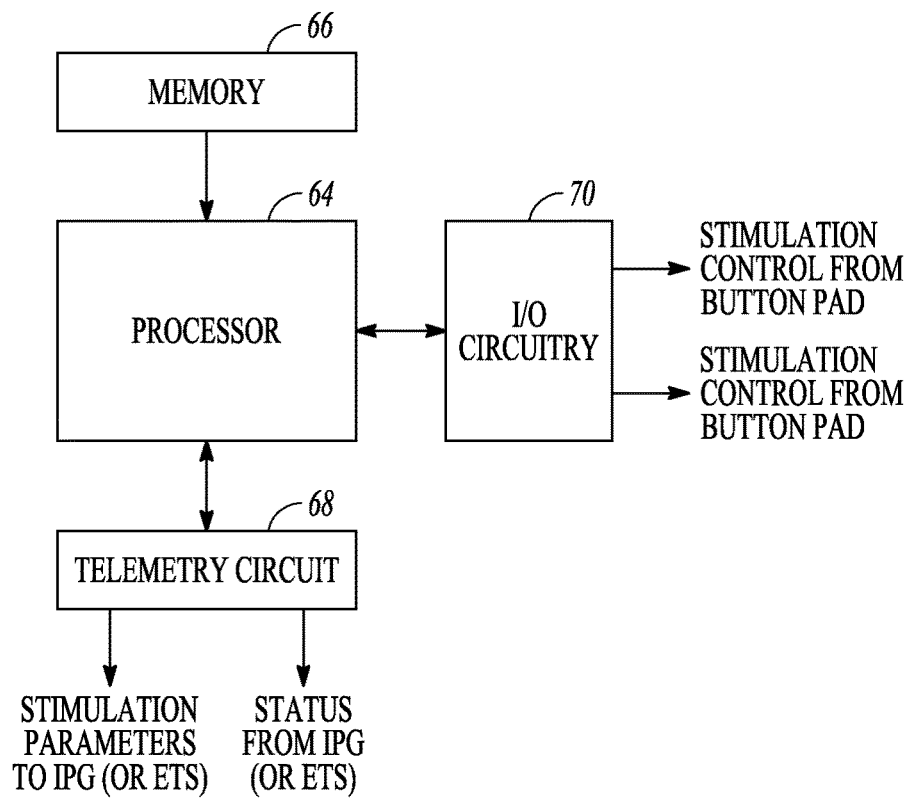
FIG. 2 illustrates, by way of example and not limitation, a block diagram of internal components of an exemplary intermediate controller as used in the neuromodulation system 100 shown in FIG. 1.

FIG. 2 illustrates, by way of example and not limitation, a block diagram of internal components of an exemplary intermediate controller 160 included in the neuromodulation system 100 as shown in FIG. 1. The intermediate controller 160 generally includes a controller/processor 64 (e.g., a microcontroller); memory 66 that stores an operating program for execution by the controller/processor 64, as well as modulation parameter sets; telemetry circuitry 68 for outputting modulation parameters to the IMD 112 or otherwise directing the IMD 112 to deliver modulation energy in accordance with the modulation parameters, and receiving status information from the IMD 112; and input/output (I/O) circuitry 70 for receiving modulation control signals from control elements and transmitting status information to a display screen on the intermediate controller 160. Further details of the functionality and internal componentry of the intermediate controller 160 are discussed in U.S. Pat. No. 6,895,280, the disclosures of which are incorporated herein by reference.

Figure 3:
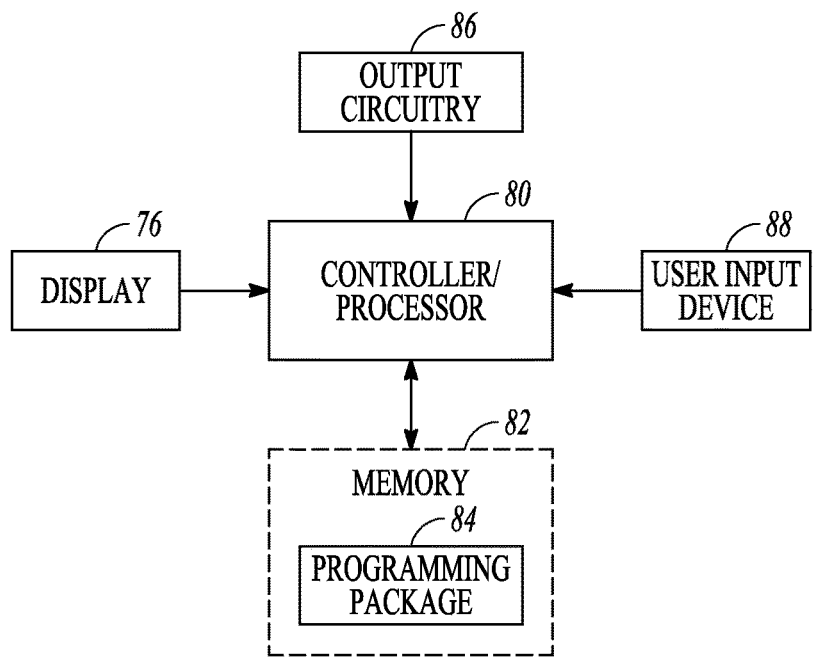
FIG. 3 illustrates, by way of example and not limitation, a block diagram of the internal components of the programmer as used in the neuromodulation system 100 shown in FIG. 1
Figure 6:
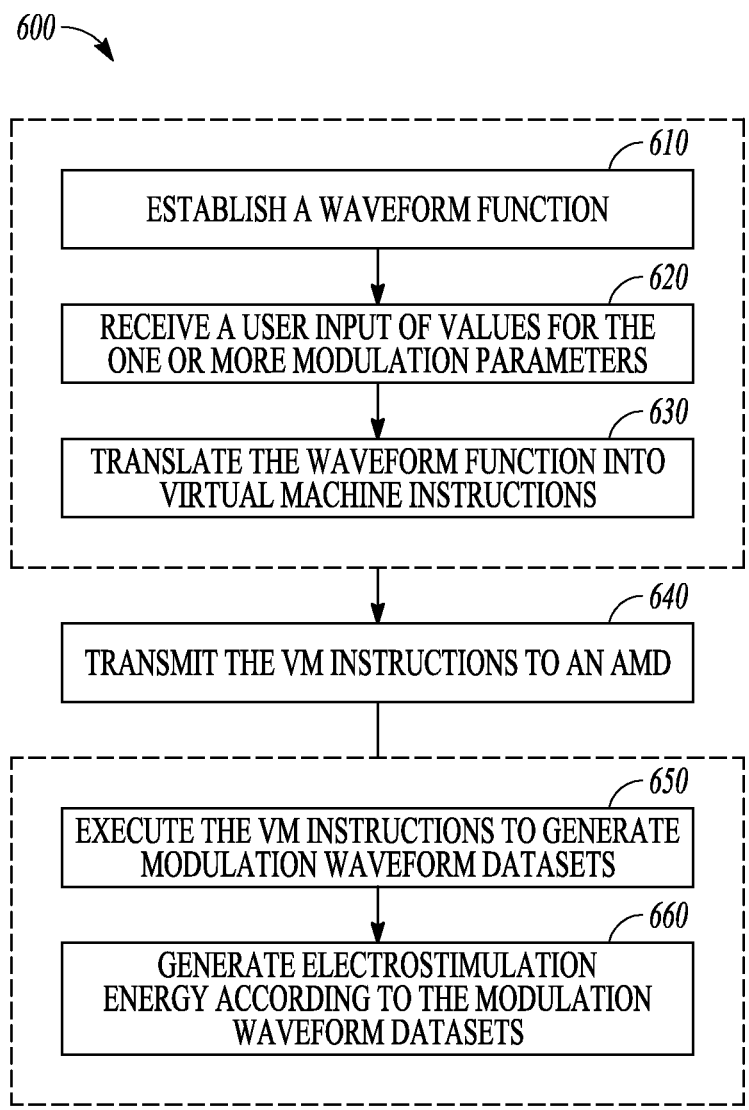
FIG. 6 illustrates, by way of example and not limitation, a method for programming a neuromodulation system to provide electrostimulation to a patient.

FIG. 3 illustrates, by way of example and not limitation, a block diagram of the internal components of the programmer 180 as used in the neuromodulation system 100 shown in FIG. 1. The programmer 180 includes a controller/processor 80 (e.g., a central processor unit (CPU)) and memory 82 that stores a stimulation programming package 84, which can be executed by the controller/processor 80 to allow the user to program the IMD 112 and intermediate controller 160. The programmer 180 further includes an output circuitry 86 for downloading one or more modulation parameters to the IMD 112 and intermediate controller 160 and for uploading one or more modulation parameters already stored in the memory 66 of the intermediate controller 160 or memory of the IMD 112. In addition, the programmer 180 further includes a user input device 88 to provide user commands. Notably, while the controller/processor 80 is shown in FIG. 6 as a single device, the processing functions and controlling functions can be performed by a separate controller and processor 64. Thus, it can be appreciated that the controlling functions as being performed by the programmer 180 can be performed by a controller, and the processing functions as being performed by the programmer 180 can be performed by a processor.

Figure 4A:
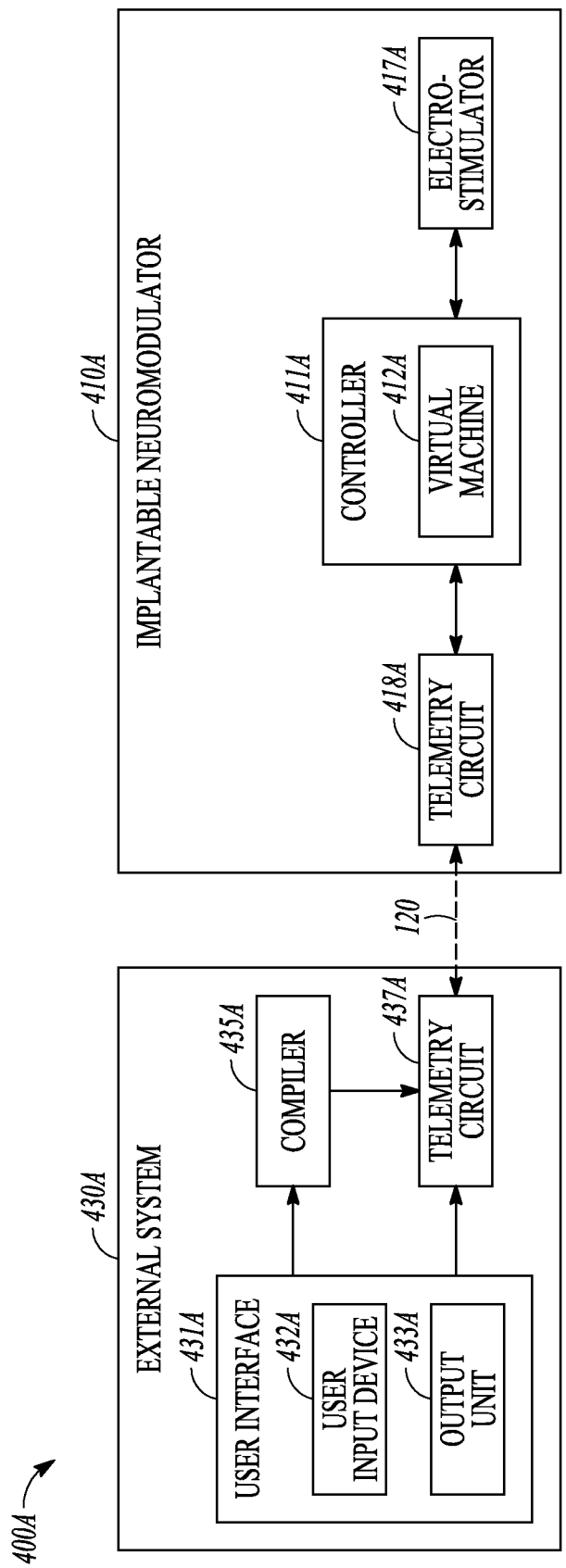
FIGS. 4A-B illustrate, by way of example and not limitation, examples of a neuromodulation system.
Figure 4B:
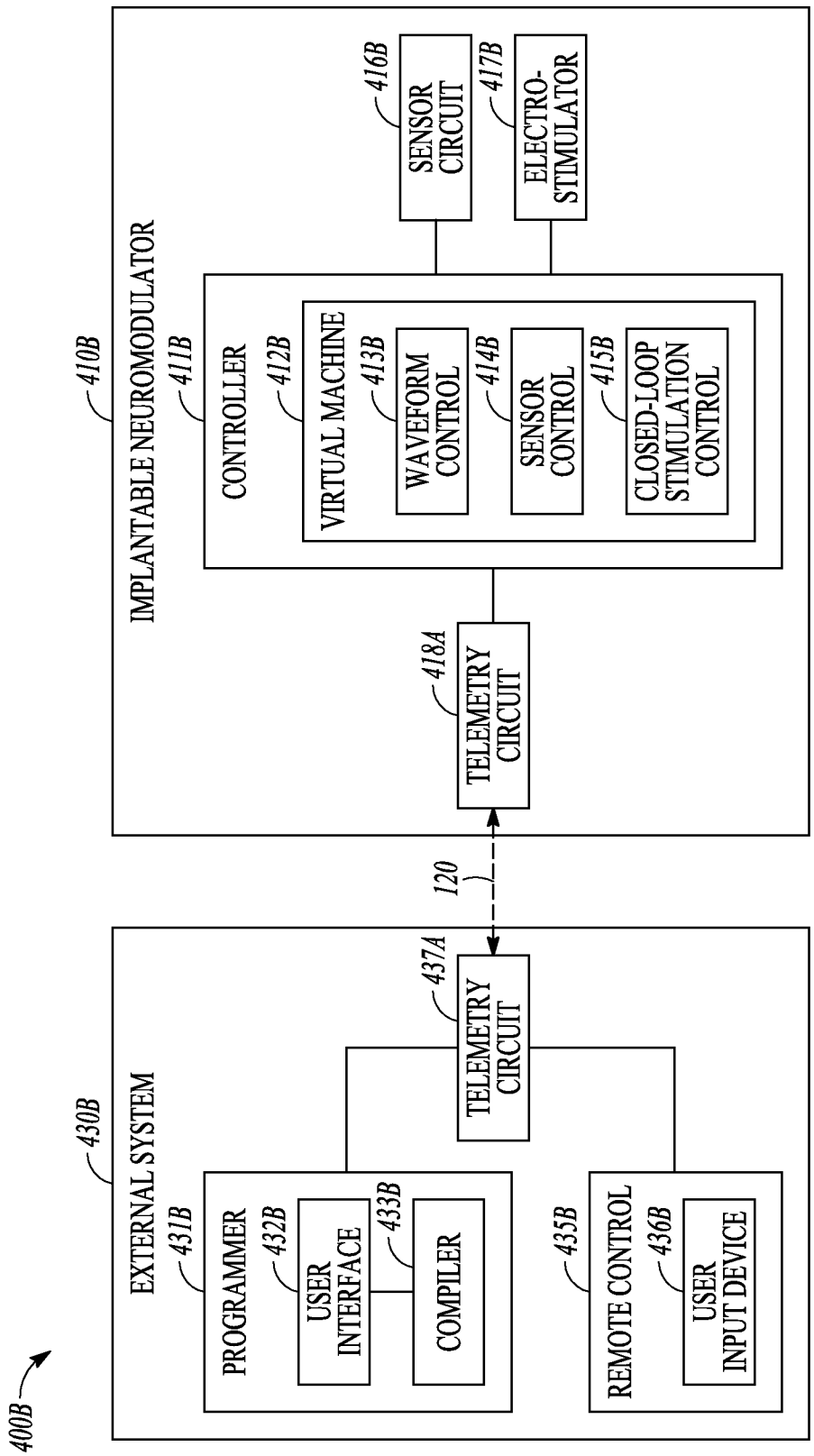

FIGS. 4A-B illustrate, by way of example and not limitation, various examples of a neuromodulation system, which may be an embodiment of the neuromodulation system 100. FIG. 4A illustrates an exemplary neuromodulation system 400A that includes an implantable neuromodulator 410A and an external system 430A, which are embodiments of the IMD 112 and the external system 130 respectively illustrated in FIG. 1. The external system 430A may be in communication with the implantable neuromodulator 410A via the communication link 120.

The external system 430A may include a user interface 431A, a compiler 435A, and a telemetry circuit 437A. The user interface 431A may be incorporated into the programmer 180 or the intermediate controller 160, or distributed between the programmer 180 and the intermediate controller 160. The user interface 431A may include a user input device 432A and an output unit 433A. Examples of the user input device 432 may include a keyboard, on-screen keyboard, mouse, trackball, touchpad, touch-screen, or other pointing or navigating devices. The output unit 433A may include a display screen. The user input device 432A may enable a system user, such as a clinician or a patient, to program one or more modulation parameters. In an example, the user input device 432A may be configured to receive from a system user a waveform function. A waveform function may define a collection of modulation programs, where each modulation program is characterized by one or more modulation parameters. One type of modulation parameter may include temporal modulation parameters, such as pulse amplitude, pulse width, pulse rate, or burst intensity. Another type of modulation parameter is morphological modulation parameter that defines one or more portions of stimulation waveform morphology, such as amplitudes of different phases or pulses of a stimulation burst. Yet another type of modulation parameter may include spatial modulation parameters such as selection of active electrodes, electrode combinations which define the electrodes that are activated as anodes (positive), cathodes (negative), and turned off (zero), and stimulation energy fractionalization which defines amount of current, voltage, or energy assigned to each active electrode and thereby determines spatial distribution of the modulation field.

In an example, a waveform function may define three member modulation programs, including a steering program, a pulse program, and a complex waveform program, which may be used when patient is under certain physiological states. Each modulation program may define a particular modulation waveform as characterized by a number of modulation parameters such as pulse amplitude, pulse width, pulse rate, burst intensity, or pulse morphological parameters. The system user may provide textual or graphical descriptions of the waveform function (including descriptions of various modulation programs) via the input device 432A. The modulation waveforms corresponding to the modulation programs, such as steering waveform, pulse waveform, and a complex waveform, may be displayed on a display screen of the output unit 433. Examples of an external system for receiving user input of waveform function are discussed below such as with reference to FIGS. 5A-B.

The user input device 432A may additionally receive, from a system user, values of the one or more modulation parameters for each member modulation program. Alternatively, when the system operates under a Modulation Magnitude Adjustment Mode (such as selected by using the intermediate controller 160), a single modulation magnitude M (rather than individual values of multiple modulation parameters) may be provided for a modulation program. The single modulation magnitude M may control an aggregate of modulation parameters according to the respectively defined parameter gain functions (PGF). For example, in a steering program, pulse amplitude $P_A$, pulse width $P_W$, and pulse rate $P_R$ may be defined as respective PGFs (f1, f2, and f3, respectively) of a single modulation magnitude M, that is, $P_A$=f1(M), $P_W$=f2(M), $P_R$=f3(M). The PGFs may be linear, piece-wise linear, or nonlinear functions. As a result, the modulation parameters such as $P_A$, $P_W$, or $P_R$ may be adjusted linearly or nonlinearly with respect to the modulation magnitude M. In an example, $P_A$ and $P_R$ may be proportional to the modulation magnitude M. By dialing up the modulation magnitude M, the stimulation intensity may be proportionally increased. A single M value may therefore be sufficient to control the steering program. Similarly, for a waveform function that includes three member modulation programs (e.g., steering program, a pulse program, and a complex waveform program), each modulation program may be controlled by respective M values, such as M=$M_1$ for controlling the steering program, M=$M_2$ for controlling the pulse program, and M=$M_3$ for controlling the complex waveform program.

The PGFs may be stored in the memory 66 of the intermediate controller 160 as shown in FIG. 2, or the memory 82 of the programmer 180 as shown in FIG. 3. A magnitude interpreter unit may translate the user input value of the modulation magnitude M into the values for the modulation parameters of each modulation program in accordance with the PGFs associated with the modulation parameters. The magnitude interpreter unit may be implemented in the processor 64 of the intermediate controller 160, or the controller/processor 80 of the programmer 180. Alternatively, the magnitude interpreter unit may be implemented in the implantable neuromodulator 410A.

In addition to defining various modulation programs, the waveform function may include instructions for other functionalities, including computing delivered energy or charge balance associated with the modulation waveform corresponding to the one or more modulation programs. In an example, the waveform function may include instructions of calculating total delivered charge per pulse or remaining charge, modifying stimulation parameter such as adding extra phases or adjusting pulse width to ensure overall charge balance, creating new pulse waveform using genetic algorithm or other sophisticated algorithms, or handling pseudo-random behavior or modulations.

The compiler 435A may be configured to translate the waveform function into VM instructions comprehensible and executable by a virtual machine 412A residing within the implantable neuromodulator 410A. The telemetry circuit 437A may establish a bi-directional communication with the implantable neuromodulator 410A. The compiled VM instructions, and the input values for the modulation parameters or a new modulation magnitude may be transmitted to the implantable neuromodulator 410A via the communication link 120.

The implantable neuromodulator 410A may include one or more of a controller 411A, an electrostimulator 417A, and a telemetry circuit 418A. The telemetry circuit 418A establishes a bi-directional communication with the external system 430A. Via the communication link 120, the telemetry circuit 418A may be configured to receive compiled VM instructions, and the input values for the modulation parameters or a new modulation magnitude.

The controller 411A is coupled to the electrostimulator 417A to control the generation and delivery of the electrostimulation energy. The controller 411A may include a virtual machine (VM) 412A, which may interpret and execute the compiled VM instructions to generate one or more modulation waveform datasets corresponding to the one or more modulation programs. The VM 412A may emulate different architectures and allow execution of software applications, such as modulation waveform creation and update, which otherwise would be executed in the dedicated firmware of the implantable neuromodulator 410A. The VM 412A may be implemented using software, hardware, or a combination thereof. In an example, the VM 412A may be implemented as a stack-based machine. In an example, the VM 412A may execute the VM instructions to generate a dataset of a multiphasic modulation waveform corresponding a modulation program.

In various occasions, neuromodulation therapy needs to be updated to meet the patient needs. The therapy may be changed by updating the one or more modulation waveform datasets, as generated by the VM 412A. This can be achieved adjusting one or more modulation parameter values or modifying the modulation waveform of a modulation program. In one example, when new values for the modulation parameters, or new modulation magnitudes, are received from the user input device 432A and transmitted to the implantable neuromodulator 410A, the new modulation parameter values or modulation magnitudes may be applied to the existing VM instructions residing in VM 412A to regenerate the modulation programs. In another example, the waveform function may be modified by the user via the external system 430A, such as by modifying one or more modulation parameters associated with one or more modulation programs. The compiler 435A may translate the modified waveform function into modified VM instructions. The modified VM instructions may be transmitted to the implantable neuromodulator 410A, and replace the existing VM instructions. The VM 412A may interpret and execute the modified VM instructions to generate one or more new modulation waveform datasets. In yet another example, both the modulation parameter value adjustment and modulation program modification may be performed to generate the new modulation waveform datasets.

The VM 412A may reside in a sandboxed environment within the controller 411A of the implantable neuromodulator 410A, such that access to the modulation-related registers is isolated from the rest of the dedicated firmware of the implantable neuromodulator 410A. The sandboxed VM 412A may be accessible only by an abstracted hardware within the implantable neuromodulator 410A. The VM 412A may selectively authorize access to one or more registers for electrostimulation therapy generation. The sandboxed virtual machine, such as the VM 412A discussed herein, may offer a number of benefits and advantages. Because the generation or modification of a waveform function is exclusively executed within the VM 412A, there is no need to access other registers of the firmware of the implantable neuromodulator 410A. The dedicated firmware may remain unchanged and agnostic to any change in modulation program, and no firmware re-validation is necessary after a change in modulation program. Additionally, with restricted interaction with the rest of the dedicated firmware and limited hardware accessibility, the VM 412A may be hardware independent, and the same VM functions may be implemented in different types and platforms of implantable systems. Furthermore, the VM 412A as such implemented may effectively protect the implantable neuromodulator 410A from inadvertent mistakes, while at the same time allowing new stimulation functions and behavior to be implemented without substantial firmware modification.

The electrostimulator 417A may be configured to generate electrostimulation energy in accordance with the one or more modulation waveform datasets produced by the VM 412A, and deliver the energy to the patient to treat pain or other neurological disorders or cardiovascular disease. In an example, the electrostimulator 417A may deliver spinal cord stimulation (SCS) via electrodes electrically coupled to the electrostimulator 417A. The electrodes may be surgically placed at a region at or near a spinal cord tissue, which may include, by way of example and not limitation, dorsal column, dorsal horn, spinal nerve roots such as the dorsal nerve root, and dorsal root ganglia. The SCS may be in a form of stimulation pulses that are characterized by pulse amplitude, pulse width, stimulation frequency, duration, on-off cycle, pulse shape or waveform, temporal pattern of the stimulation, among other stimulation parameters. Examples of the stimulation pattern may include burst stimulation with substantially identical inter-pulse intervals, or ramp stimulation with incremental inter-pulse intervals or with decremental inter-pulse intervals. In some examples, the frequency or the pulse width may change from pulse to pulse. The electrostimulator 417A may additionally or alternatively deliver electrostimulation to other target tissues such as peripheral nerves tissues. The electrostimulator 417A may deliver transcutaneous electrical nerve stimulation (TENS) via detachable electrodes that are affixed to the skin. In another example, the electrostimulator 417A may deliver deep brain stimulation (DBS) via electrodes surgically placed at a brain tissue. In yet another example, the electrostimulator 417A may deliver a cardiac stimulation therapy or a neural stimulation therapy to treat a cardiovascular disease.

FIG. 4B illustrate an exemplary neuromodulation system 400B, which may be a variant of the neuromodulation system 400A illustrated in FIG. 4A. The neuromodulation system 400B may include an implantable neuromodulator 410B and an external system 430B in communication with the implantable neuromodulator 410B via the communication link 120. The external system 430B may include a programmer 431B, a remote control unit 435B, and telemetry circuit 437A. The user interface 431A and the compiler 435A in the external system 430A as illustrated in FIG. 4A may be distributedly implemented between a programmer 431B and a remote control unit 435B.

The programmer 431B, which may be an embodiment of the programmer 180 of the neuromodulation system 100 in FIG. 1, may include a user interface 432B and a compiler 433B. The user interface 432B, which may be an embodiment of the user interface 431A shown in FIG. 4A, may receive from a system user a waveform function via the user input device 432A. As previously discussed with reference to FIG. 4A, the waveform function, including descriptions of various modulation programs, may be provided by the system user as textual or graphical description via the user input device. The compiler 433B, which may be an embodiment of the compiler 435A shown in FIG. 4A, may translate the waveform function into VM instructions comprehensible and executable by a VM 412B residing in the implantable neuromodulator 410B. The remote control 435B, which may be an embodiment of the intermediate controller 160 of the neuromodulation system 100 in FIG. 1, may receive from a system user to provide programming values for the modulation parameters of the waveform function via the user input device 436B.

The programmer 431B and the remote control 435B may be configured to be operated by different users. In an example, the programmer 431B may be accessible to healthcare professionals, while the remote control 435B may be a portable device accessible to patient. The distributed implementation as illustrated in FIG. 4B may add flexibility to different levels of control of the generation or modification of modulation waveforms and the electrostimulation therapy. For example, a clinician may use the programmer 431B to create or modify one or more modulation programs included in the waveform function. A patient may use the remote control 435B, in an ambulatory setting, to provide or adjust modulation parameter values or a single modulation magnitude that concurrently controls an aggregate of modulation parameters within a modulation programs.

The implantable neuromodulator 410B may receive from the external system 430B the compiled VM instructions generated at the programmer 431B and the input values for the modulation parameters or a new modulation magnitude generated at the remote control 435B, through the telemetry circuits 437A and 418B and via the communication link 120. The implantable neuromodulator 410B includes a sensor circuit 416B, a controller 411B, and an electrostimulator 417A.

The sensor circuit 416B may be coupled to electrodes or various types of ambulatory sensors associated with the patient, and sense physiological or functional signals from the patient. Examples of the physiological signals may include cardiac, hemodynamic, pulmonary, neural, or biochemical signals, among others. Examples of the functional signals may include patient posture, gait, balance, or physical activity signals, among others. In various examples, an accelerometer may be used to detect an activity intensity or activity duration. A tilt switch, an accelerometer, or a thoracic impedance sensor may be used to detect posture or position. Gyroscope, magnetoresistive sensors, inclinometers, goniometers, electromagnetic tracking system (ETS), sensing fabric, force sensor, strain gauges, and sensors for electromyography (EMG) may be used to measure motion and gaits.

The controller 411B may include a virtual machine (VM) 412B. The VM 412B, which may be a variant of the VM 412A shown in FIG. 4A, may include a plurality of control modules, including a waveform control 413B, a sensor control 414B, and a closed-loop stimulation control 415B. The control modules may be implemented using hardware, software, firmware, or combinations thereof. The waveform control 413B may interpret and execute the compiled VM instructions to generate one or more modulation waveform datasets corresponding to the one or more modulation programs. In a similar fashion as previously discussed with reference to VM 412A, the VM 412B, through the waveform control 413B, may generate new modulation programs with modified modulation waveforms. The new modulation programs may be generated by modifying the waveform programs at the programmer 431B, or the modulation parameter values or the modulation magnitude at the remote control 435B.

The sensor control 414B and the closed-loop stimulation control 415B provide additional capability of the VM 412B to flexibly control functionalities of the implantable neuromodulator 410B, other than the generation or update of modulation waveform, in a sandboxed environment isolated from the rest of the firmware of the implantable neuromodulator 410B. Under the sensor control 414B, the programmer 431B or the remote control 435B may interrogate the implantable neuromodulator 410B and request sensor data acquired by the sensor circuit 416B. The request may be compiled into VM instructions by the compiler 433B. The controller 411B may interpret the instructions and forward it to the VM 412B. The VM 412B may execute the VM instructions, and apply appropriate functions to fetch the sensor data, and wait for a response to communicate the sensor data to the interrogating device (e.g., the programmer 431B or the remote control 435B) in the external system 430B. The sensor data may be displayed on a display screen of the interrogating device, or be used in a process such as data processing at the external system 430B.

Under the closed-loop stimulation control 415B, a feedback control function may be executed in the VM 412B to determine appropriate values for one or more modulation parameters based on the sensor data from the sensor circuit 416B. In an example, the sensor circuit 416B may sense physiological or functional signals in response to the electrostimulation therapy. The waveform function may include instructions for modifying one or more modulation programs based on the sensed physiological or functional signals. In an example, the controller 411B may include a pain analyzer circuit configured to generate a pain score from the sensed physiological or functional signals. The pain score provides information about onset, intensity, severity, duration, or patterns of pain perceived by the patient, and may be indicative of efficacy of the neuromodulation therapy for pain relief. The pain score may be computed as a weighted combination of signal metrics generated from physiological or functional signals. The pain score, represented as a numerical or categorical value, may quantify the patient's overall pain symptom. The closed-loop stimulation control 415B may use the pain score as feedback input, execute the feedback control function, and determine proper adjustment of the modulation parameters.

The feedback control function may be designed and provided by a user via the programmer 431B. The feedback control function may be translated into VM instructions by the compiler 433B, and transmitted to the implantable neuromodulator 410B for execution by the VM 412B. When new sensor data become available, periodically at a user-specified interval (e.g., every 100 milliseconds) or upon receiving a command, the VM instructions for feedback control function may be executed by applying the new sensor data. The modulation parameters may be generated and used for updating the waveform function. The waveform control 413B may then generate the one or more modulation waveform datasets in accordance with the updated waveform function. The electrostimulator 417A may use the one or more modulation waveform datasets to generate and deliver the electrostimulation energy.

In some examples, the neuromodulation system 400A or 440B may each include at least one computer-readable storage medium physically modified to encode instructions of the specific operation. The instructions stored in the at least one computer-readable storage medium, when executed by external system 430A or 430B, may cause the corresponding external system 430A or 430B to perform various operations as discussed above. For example, the instructions may cause the user interface 431A or 432B to receive the waveform function and values for the one or more modulation parameters of the one or more modulation programs. The instructions may cause the compiler 435A or 433B to translate the waveform function into VM instructions. The instructions may additionally cause the telemetry circuit 437A to transmit the VM instructions to the IMD 410A or 410B.

Figure 5A:
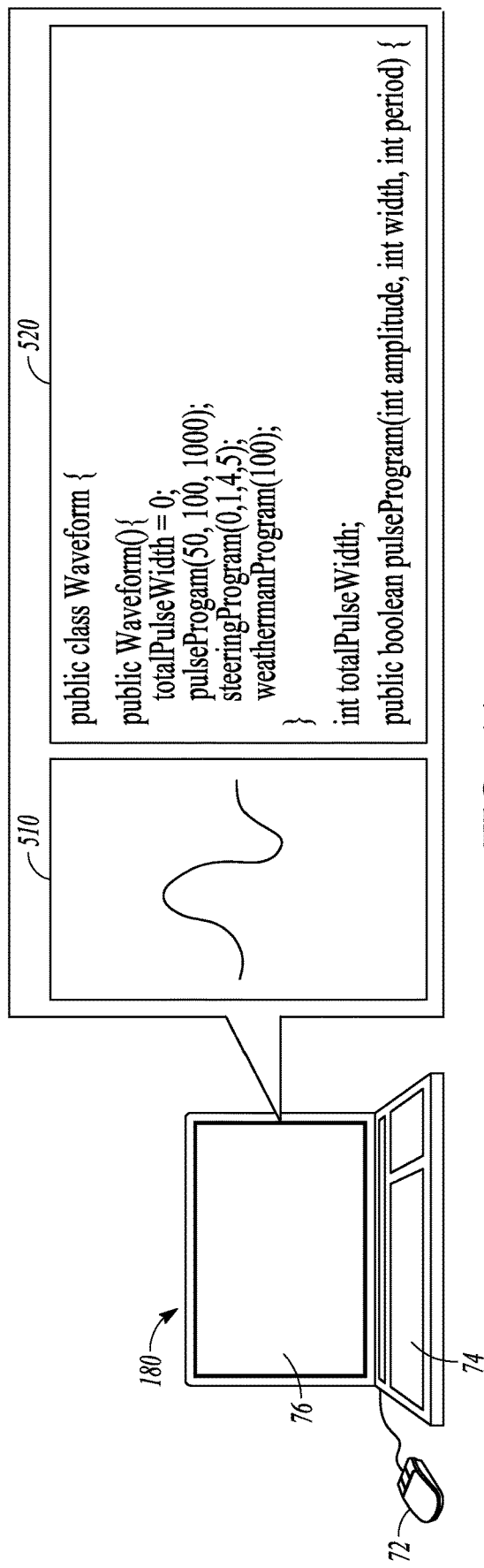
FIGS. 5A-B illustrate, by way of example and not limitation, a diagram of an external system for receiving user input of a waveform function.
Figure 5B:
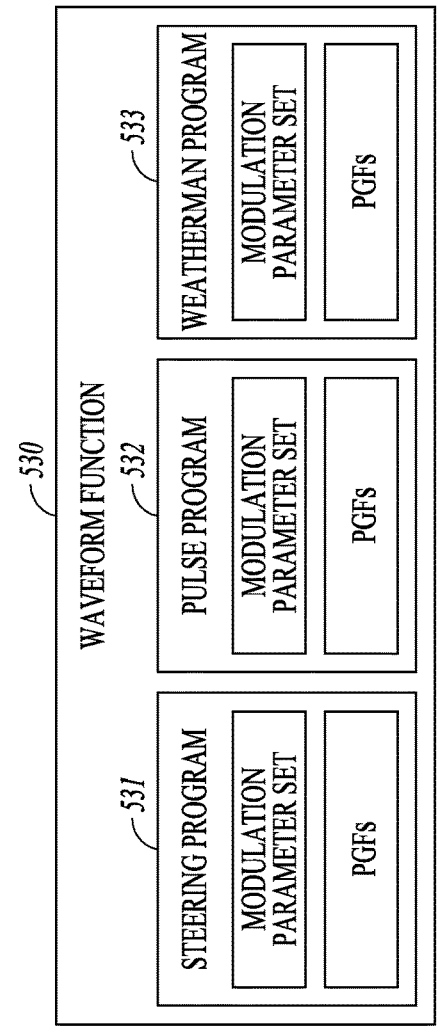

FIGS. 5A-B illustrates, by way of example and not limitation, a diagram of an external system for receiving user input of a waveform function. As illustrated in FIG. 5A, the external system includes the programmer 180 used in the neuromodulation system 100 as illustrated in FIG. 1. Alternatively, an intermediate controller 160 or other external monitoring device may be used. The programmer 180 may include input devices including a mouse 72 and keyboard 74, and an output unit including a display 76. Via the input device, a user may provide a graphical representation 510 or textual description 520 of the waveform function. Examples of textual description 520 may include a code segment of a programming language, pseudo code, or otherwise a set of machine-comprehensible instructions. When multiple modulation programs are included in the waveform function, modulation waveforms of the modulation programs may be textually or graphically designed using the input device. The graphical or textual description of the waveform function may be displayed at the display screen 76. The user may interactively modify, graphically or textually, the waveform function, such as by adjusting a modulation parameter for a particular member modulation waveform.

FIG. 5B illustrates and example of the waveform function 530, which may include a steering program 531, a pulse program 532, and a complex waveform program 533. Each modulation program contains a corresponding modulation waveform in a form of either textual or graphical representation. The member modulation waveform may be described using a corresponding modulation parameter set, which may include one or more modulation parameters such as pulse amplitude, pulse width, pulse frequency, burst intensity, or morphological parameters, among others. The member modulation programs may each additionally include parameter gain functions (PGFs) that define the values of the one or more modulation parameters with respect to a single modulation magnitude M. The PGFs may be linear, piece-wise linear, or non-linear functions. The PGFs may be designed using graphical or textual descriptions via the input device. The PGFs thus created may be stored in the memory of the intermediate controller 160 as shown in FIG. 2, or the memory 82 of the programmer 180 as shown in FIG. 3.

The waveform function, including graphical or textual descriptions of the modulation parameters or the PGFs associated with member modulation programs, may be compiled by the compiler 435A or 432B to produce compiled VM instructions. The VM instructions may be transferred to the implantable neuromodulator 410A or 410B, executed at the VM 412A or 412B to generate the one or more modulation waveform datasets corresponding to the modulation programs. The electrostimulator 417A may generate stimulation therapy according to the one or more modulation waveform datasets.

FIG. 6 illustrates, by way of example and not limitation, a method 600 for programming a neuromodulation system to provide electrostimulation to a patient. The method 600 may be implemented in a medical system, such as the neuromodulation system 400A or 400B. The method 600 may be used to provide neuromodulation therapy, such as SCS, DBS, PNS, FES, or VNS therapies, to treat pain or various neurological disorders. The method 600 may additionally or alternatively be used to provide electrostimulation therapy to treat a cardiovascular disease or other health disorders.

The method 600 may be implemented and executed by an ambulatory device such as the IMD 112 or the implantable neuromodulator 410A or 410B, or executed by an external programmer or remote server-based patient management system communicatively coupled to the ambulatory device, such as the external systems 130, 430A, or 430B. The method 600 may be distributedly implemented between an ambulatory device and a communicatively coupled external device. In a non-limiting example as illustrated in FIG. 6, steps 610-630 may be implemented and executed in an external system, and steps 650-660 may be implemented and executed in an implantable device.

The method 600 begins at step 610, where a waveform function may be established by a user, such as by using the programmer 180 or the programmer 430 or other external programming devices. The waveform function defines one or more modulation programs, each of which may be characterized by one or more modulation parameters. Examples of the modulation parameters may include pulse amplitude, pulse width, pulse rate, burst intensity, or morphological parameters for one or more portions of stimulation waveform morphology. The modulation parameters may include spatial modulation parameters such as selection of active electrodes, electrode combinations, or stimulation energy fractionalization. The waveform function may be established as a textual or graphical description of the waveform function (including descriptions of various modulation programs), such as those illustrated in FIGS. 5A-B. The established waveform function may be display on a screen. The user may interactively modify, graphically or textually, the waveform function, such as by adjusting a modulation parameter for a particular member modulation waveform.

The waveform function may include, for each member modulation program, parameter gain functions (PGF) that define an aggregate of modulation parameters with respect to a single modulation magnitude M. The PGFs may be linear, piece-wise linear, or non-linear functions. The PGFs may be created using graphical or textual descriptions. In some examples, the waveform function may include instructions for computing delivered energy or charge balance associated with the one or more modulation waveform datasets corresponding to the one or more modulation programs.

At 620, user input of values for the one or more modulation parameters of the one or more modulation programs may be received, such as from a user input device on the intermediate controller 160 or the remote control 435B. When the waveform function defines multiple member modulation programs, modulation parameter values for each member modulation program may be provided to the system. Alternatively, when the PGFs are used to define an aggregate of modulation parameters of a modulation program, a single modulation magnitude (rather than values of multiple modulation parameters) may be provided for a modulation program. The modulation magnitude may control the modulation parameters through the PGFs.

At 630, the waveform function may be translated into virtual machine (VM) instructions comprehensible and executable by a virtual machine such as the VM 412A or VM 412B residing in an implantable device. At 640, the VM instructions may be transmitted to an ambulatory medical device (AMD) such as an implantable neuromodulator device, where the VM instructions may be executed at 650 by a virtual machine such as the VM 412A or VM 412B to generate one or more modulation waveform datasets corresponding to the one or more modulation programs. In an example, execution of the VM instructions may yield a dataset of a multiphasic modulation waveform corresponding to a modulation program. The VM instructions may be executed when new values for the modulation parameters, or a new modulation magnitude is received and forwarded to the implantable device. In some examples, the waveform function may be modified by the user, such as by modifying one or more modulation parameters associated with one or more modulation programs. The modified waveform function may be re-compiled at 630 into modified VM instructions, which are transmitted to the AMD at 640 to replace the existing VM instructions, and get executed to generate one or more new modulation waveform datasets.

At 660, electrostimulation energy may be generated according to the modulation waveform datasets. The electrostimulation energy may be used to treat chronic pain or other neurological disorders or cardiovascular disease. In an example, spinal cord stimulation (SCS) may be delivered via electrodes surgically placed at a region at or near a spinal cord tissue. In another example, transcutaneous electrical nerve stimulation (TENS) may be delivered via detachable electrodes affixed to the skin. In yet another example, deep brain stimulation (DBS) may be delivered via electrodes surgically placed at a brain tissue. In some examples, a cardiac stimulation therapy or a vagus nerve stimulation therapy may be delivered to treat a cardiovascular disease such as heart failure.

Other than the modulation programs that define the modulation waveforms, other device functionalities, such as sensor data inquiry and interrogation and close-loop control of modulation waveforms, may similarly be created and translated into VM instructions for execution by the VM in the implantable device. Controlling device behavior through the VM is advantageous as the VM as discussed in this document provides a safe sandboxed environment isolated from the rest of the dedicated firmware of the implantable device. In an example, the implantable device may include sensor circuit configured to sense multiple physiological signals. The sensed physiological signal may be used as input to a closed-loop neuromodulation system. A user may request sensed physiological signals be transmitted to the external system for display or for further data processing at the external system. At 610, an interrogation request may be established at the interrogating device, such as the programmer 431B or the remote control 435B. The interrogation request may be compiled into VM instructions at 630, and transmitted to the IMD at 640. The VM instructions corresponding to sensor data request may be executed at 650, and the sensor data may be fetched and transmitted back to the interrogating device for display or further processing.

Figure 7:
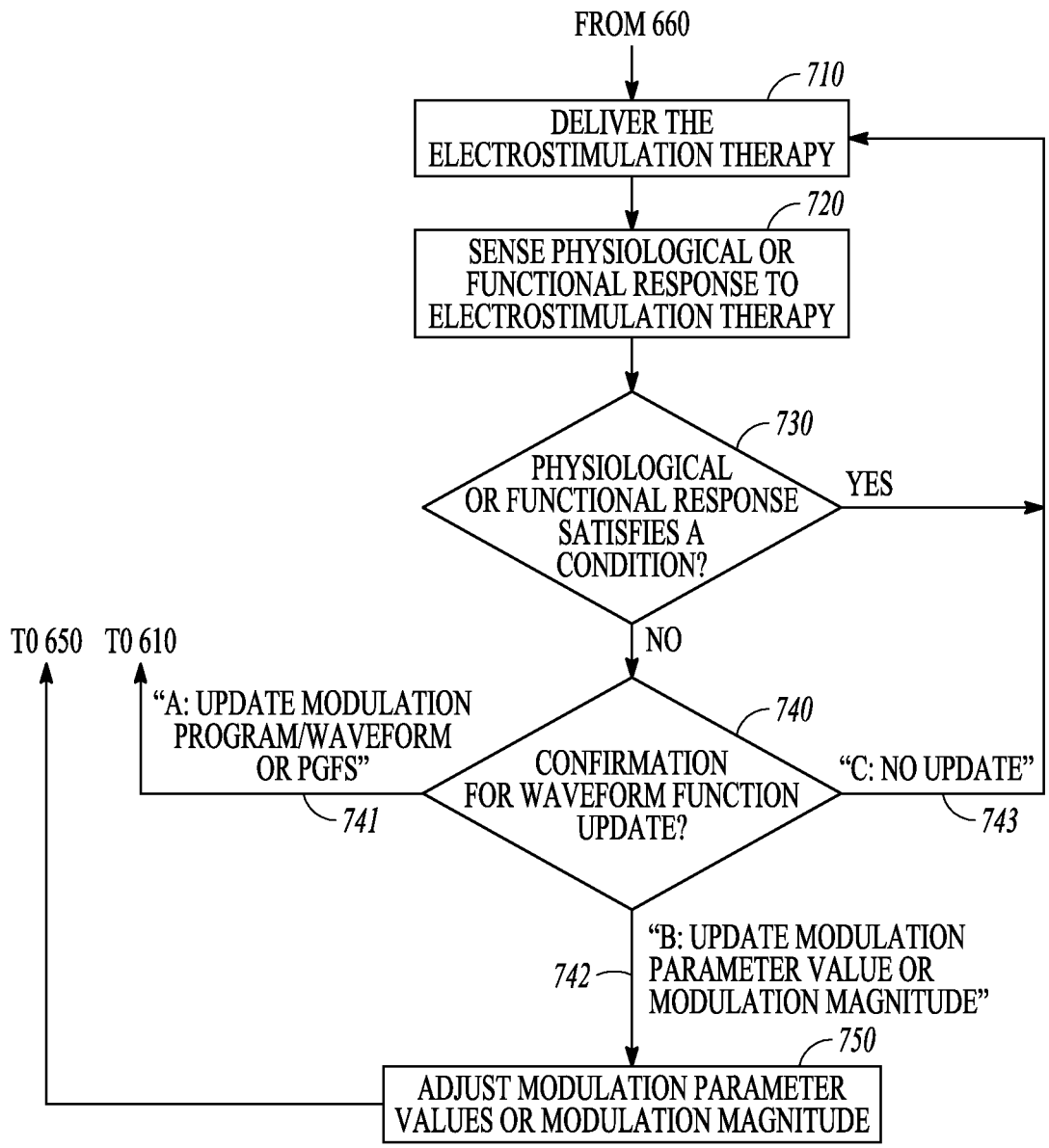
FIG. 7 illustrates, by way of example, a method for programming a neuromodulation system to provide closed-loop electrostimulation to a patient.

FIG. 7 illustrates, by way of example, a method 700 for programming a neuromodulation system to provide closed-loop electrostimulation to a patient. The method 700 may be implemented in a medical system, such as the neuromodulation system 400B, and provide neuromodulation therapy or cardiac stimulation therapy. The method 700 may be a variant of the method 600, and includes additional steps directed to receiving sensor feedback to electrostimulation therapy and adjust one or more modulation programs based at least on the sensor feedback.

The method 700 begins at 710 where electrostimulation therapy may be administered by delivering the electrostimulation energy generated at 660 of the method 600 to a target tissue. At 720, physiological and functional signals in response to electrostimulation therapy may be sensed such as via the sensor circuit 416B coupled to electrodes or ambulatory sensors associated with the patient, as illustrated in FIG. 4B. The sensor circuit may sense physiological or functional signals before, during, or after the therapy deliver. Examples of the physiological signals may include cardiac, pulmonary, or neural signals, such as, by way of example of limitation, electrocardiograph (ECG) or intracardiac electrogram, heart rate signal, heart rate variability signal, cardiovascular pressure signal, or heart sounds signal, respiratory signal, a thoracic impedance signal, or a respiratory sounds signal, or neural activity signal. The physiological signals may also include blood chemistry measurements or biomarkers. Examples of the functional signals may include patient posture, gait, balance, physical activity signals, or signals indicating sleep or awake state, among others. Such functional signals may responsively co-variate with a pain episode. In an example, the functional signals may be sensed using accelerometer sensors.

A plurality of signal metrics may be generated from the sensed physiological or functional signals. At 730, the signal metrics may be compared a specified condition (such as a threshold value) to determine if the delivered electrostimulation therapy has achieved a desirable outcome. In an example, a pain score may be computed as a weighted combination of signal metrics generated from physiological signals sensed from multiple sensors. Such a multi-sensor indicated pain score, represented as a numerical or categorical value, may quantify the patient's overall pain symptom. The pain score may be indicative of efficacy of the neuromodulation therapy for pain relief.

If the physiological or functional response satisfies the specified condition such as reduced pain or improved physiological or functional outcome, the therapy is deemed effective; and no attempt of therapy adjustment is made. The existing therapy may be continued at 710 according to the programmed waveform function. If at 730 the physiological or functional response fails to satisfy the specified condition, the existing therapy is indicated to fail to achieve desirable therapeutic outcome, and a user may be prompted to modify the existing therapy at 740 based on the sensor feedback. As the electrostimulation therapy is determined based at least on the VM instructions for modulation waveform function, as well as the values for the modulation parameters, therapy modification may be achieved by adjusting the modulation parameter values, or by reconfiguring and modulation waveform function. If at 740 a first option 741 is selected to update modulation program or waveform, then the process returns to step 610 to re-establish a new waveform function, which may include updating one or more modulation parameters of a modulation program. The modified waveform function then may be re-compiled at 630 to produce modified VM instructions, which may be transmitted to the AMD for execution at the VM to generate one or more new modulation waveform datasets. If at 740 a second option 742 is selected to update modulation parameter value, then the VM instructions for modulation waveform function remain effective and are kept unchanged at the VM. One or more modulation parameter values may be adjusted at 750. The process then continues at 650 where the newly adjusted modulation parameter values may be applied to the existing VM instructions to generate one or more new modulation waveform datasets, and modified electrostimulation therapy can be generated accordingly at 660. If at 740 a third option 743 is selected not to update the existing waveform function, then neither the modulation programs nor the modulation parameter values would be changed. The existing neuromodulation therapy may be continued at 710 according to the programmed waveform function.

In some examples, the waveform function may include PGFs that define an aggregate of modulation parameters with respect to a single modulation magnitude, and the one or more modulation waveform datasets are generated using the VM instructions corresponding to the PGFs, as well as the modulation magnitudes for the modulation programs. At 740, the user may select from a first option 741 of modifying one or more PGFs, a second option 742 of changing a modulation magnitude, or a third option of keeping the existing PGFs and the modulation magnitude. By selecting the first option 741, PGFs of one or more modulation parameters associated with a modulation program, such as the pulse amplitude, pulse width, or pulse rate, may be updated at step 610 to re-establish a new waveform function.

The modified waveform function then needs to be re-compiled at 630 to produce modified VM instructions execution to generate one or more new modulation waveform datasets. By selecting the second option 742, existing PGFs will remain effective at the VM in the AMD, but the modulation magnitudes for one or more modulation programs may be adjusted at 750. For example, an increase in the modulation magnitude may produce a proportionally stronger perceived modulation effect, when the PGFs are linear or nonlinear growth functions. The process then continues at 650 where the existing VM instructions for PGFs may be executed, using the adjusted modulation magnitude, to generate one or more new modulation waveform datasets.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using combinations or permutations of those elements shown or described.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The scope of the invention should be determined with reference to the appended claims, along with the full scope of equivalents to which such claims are entitled.

What is claimed is:

1. A system for providing electrostimulation to a patient, the system comprising:
   an ambulatory medical device (AMD) including a virtual machine (VM) and an electrostimulator; and
   at least one computer-readable storage medium including instructions executable on an external system communicatively coupled to the AMD, the external system including a user interface, a compiler, and a telemetry circuit;
   wherein the instructions, when executed by the external system:
      enable the user interface to receive (1) a waveform function in a form of computer code or a graph, the waveform function defining one or more modulation programs characterized by respective one or more modulation parameters, and (2) a user input of values for the one or more modulation parameters of the one or more modulation programs;
      cause the compiler to translate the waveform function into VM instructions; and
      cause the telemetry circuit to transmit the VM instructions to the AMD;
      wherein the VM of the AMD is configured to execute the VM instructions to generate respective one or more modulation waveform datasets corresponding to the one or more modulation programs, and the electrostimulator is configured to generate electrostimulation therapy according to the one or more modulation waveform datasets.

2. The system of claim 1, wherein:
   the external system is configured to modify the waveform function or adjust the values for the one or more modulation parameters, and the compiler is configured to translate the modified waveform function into modified VM instructions; and
   the VM of the AMD is further configured to update the one or more modulation waveform datasets by executing the modified VM instructions or by using the adjusted values for the one or more modulation parameters.

3. The system of claim 1, wherein the external system further includes:
   a device programmer including the user interface to receive the waveform function and the compiler to translate the waveform function into the VM instructions; and
   a remote control device including a user input device to receive the user input of the values for the one or more modulation parameters.

4. The system of claim 1, wherein the electrostimulator is configured to generate a spinal cord stimulation therapy or a deep brain stimulation therapy.

5. The system of claim 1, wherein the electrostimulator is configured to generate a cardiac stimulation therapy or a neural stimulation therapy to treat a cardiovascular disease.

6. The system of claim 1, wherein the user interface includes a display configured to textually or graphically display the waveform function.

7. The system of claim 1, wherein the waveform function further includes instructions for computing delivered energy or charge balance associated with the one or more modulation waveform datasets corresponding to the one or more modulation programs.

8. The system of claim 1, wherein:
   the AMD further includes a sensor circuit configured for sensing a physiological response to delivery of the electrostimulation therapy according to the one or more modulation waveform datasets; and
   the waveform function further includes instructions for modifying one or more modulation programs based on the sensed physiological response.

9. The system of claim 8, wherein:
   the AMD further includes a pain analyzer configured to generate a pain score using the sensed physiological response; and
   the waveform function further includes instructions for modifying one or more modulation programs based on the generated pain score.

10. The system of claim 1, wherein the user interface is configured to receive a user input of a modulation magnitude representing a level of stimulation intensity, wherein the values for the one or more modulation parameters are determined based on the modulation magnitude.

11. The system of claim 10, wherein the external system further comprises a magnitude interpreter unit configured to translate the modulation magnitude into the values for the one or more modulation parameters using a plurality of gain functions respectively defining values of the one or more modulation parameters corresponding to a plurality of modulation magnitudes.

12. The system of claim 11, wherein the magnitude interpreter unit is at least partially included in the external system or the AMD.

13. The system of claim 1, wherein the VM is further configured to selectively authorize access to one or more registers for electrostimulation therapy generation.

14. A method for providing electrostimulation to a patient via an ambulatory medical device (AMD) communicatively coupled to an external system, the method comprising:
   establishing a waveform function via an external system, the waveform function having a form of computer code or a graph and defining one or more modulation programs characterized by respective one or more modulation parameters;
   receiving a user input of values for the one or more modulation parameters of the one or more modulation programs;
   translating, via a compiler included in the external system, the waveform function into virtual machine (VM) instructions;
   transmitting the VM instructions to the AMD;
   executing the VM instructions to generate respective one or more modulation waveform datasets corresponding to the one or more modulation programs; and
   generating electrostimulation therapy via the AMD according to the one or more modulation waveform datasets.

15. The method of claim 14, further comprising modifying the waveform function or adjusting the values for the one or more modulation parameters, and updating the one or more modulation waveform datasets using (1) VM instructions translated from the modified waveform function or (2) adjusted the values for the one or more modulation parameters.

16. The method of claim 14, wherein the electrostimulation therapy includes at least one of a spinal cord stimulation therapy, a deep brain stimulation therapy, a cardiac stimulation therapy, or a vagus nerve stimulation therapy.

17. The method of claim 14, further comprising displaying textually or graphically the one or more modulation programs.

18. The method of claim 14, wherein the established waveform function further includes instructions for computing delivered energy or charge balance associated with the one or more modulation waveform datasets corresponding to the one or more modulation programs.

19. The method of claim 14, further comprising:
   sensing a physiological response to a delivery of the electrostimulation therapy according to the one or more modulation waveform datasets; and
   generating a pain score using the sensed physiological response;
   wherein the waveform function further includes instructions for modifying one or more modulation programs based on the generated pain score.

20. The method of claim 14, wherein receiving a user input of values for the one or more modulation parameters includes receiving a modulation magnitude representing a level of stimulation intensity, where the values for the one or more modulation parameters are determined based on the modulation magnitude.

* * * * *